United States Patent
Choi

(10) Patent No.: US 10,203,949 B2
(45) Date of Patent: Feb. 12, 2019

(54) SYSTEM AND METHOD FOR PROVIDING SOFTWARE UPDATES

(71) Applicant: HYUNDAI MOTOR COMPANY, Seoul (KR)

(72) Inventor: Kee Hoon Choi, Suwon-si (KR)

(73) Assignee: HYUNDAI MOTOR COMPANY, Seoul (KR)

( * ) Notice: Subject to any disclaimer, the term of this patent is extended or adjusted under 35 U.S.C. 154(b) by 0 days.

(21) Appl. No.: 15/352,005

(22) Filed: Nov. 15, 2016

(65) Prior Publication Data
US 2017/0329599 A1    Nov. 16, 2017

(30) Foreign Application Priority Data
May 11, 2016    (KR) .......................... 10-2016-0057340

(51) Int. Cl.
*G06F 8/61*    (2018.01)
*G06F 8/65*    (2018.01)

(52) U.S. Cl.
CPC . *G06F 8/65* (2013.01); *G06F 8/61* (2013.01)

(58) Field of Classification Search
CPC .................................... G06F 8/65; G06F 8/61
USPC ....................................... 717/168, 170, 171
See application file for complete search history.

(56) References Cited

U.S. PATENT DOCUMENTS

| | | | | |
|---|---|---|---|---|
| 6,643,506 | B1 * | 11/2003 | Criss ......................... | G06F 8/65 455/418 |
| 6,820,259 | B1 * | 11/2004 | Kawamata ................ | G06F 8/61 717/173 |
| 2001/0029178 | A1 * | 10/2001 | Criss ......................... | G06F 8/65 455/419 |
| 2005/0050538 | A1 * | 3/2005 | Kawamata ................ | G06F 8/61 717/168 |
| 2006/0106806 | A1 * | 5/2006 | Sperling ................... | G06F 8/65 |
| 2010/0107150 | A1 * | 4/2010 | Kamada .................... | G06F 8/65 717/170 |
| 2011/0320089 | A1 * | 12/2011 | Lewis ...................... | G01C 21/32 701/29.6 |

FOREIGN PATENT DOCUMENTS

| | | |
|---|---|---|
| JP | 2006-340196 A | 12/2006 |
| KR | 10-2004-0088134 A | 10/2004 |
| KR | 10-2006-0041027 A | 5/2006 |
| KR | 10-0739135 B1 | 7/2007 |

(Continued)

*Primary Examiner* — Phillip H Nguyen
(74) *Attorney, Agent, or Firm* — McDermott Will & Emery LLP

(57) ABSTRACT

A system for providing a software update includes a server in which software updates are registered, and a terminal for receiving version information of a software update from the server and performing a software update on the basis of the received version information of the software update, wherein the server includes a version information checking unit for collecting version information of software temporarily stored in the terminal or version information of software installed in the terminal and comparing the version information of the temporarily stored software or the version information of the installed software with the version information of the software update to determine whether to transmit the software update to the terminal.

17 Claims, 3 Drawing Sheets

(56) References Cited

FOREIGN PATENT DOCUMENTS

| KR | 10-2009-0120740 A | 11/2009 |
| KR | 10-1048435 B1 | 7/2011 |
| KR | 10-2015-0075617 A | 7/2015 |

* cited by examiner

SYSTEM AND METHOD FOR PROVIDING SOFTWARE UPDATES

CROSS REFERENCE TO RELATED APPLICATION

This application claims the benefit of Korean Patent Application No. 10-2016-0057340, filed on May 11, 2016, which is hereby incorporated by reference as if fully set forth herein.

TECHNICAL FIELD

The present disclosure relates to a system and method for providing software updates and, more particularly, to a software update providing system and method for providing efficient software updates to a terminal included in a vehicle.

BACKGROUND

As various terminals (electronic control unit, AVN, etc.) are mounted in vehicles, users often desire or are required to update software installed in vehicles. In addition, drivers may have to drive their cars to visit designated repair shops or centers in order to update the software. Accordingly, there is a need for methods of updating software installed in vehicles through wired and/or wireless connections.

Software updates through wireless connection is a method useful to simultaneously update the software installed in multiple vehicles. However, to update software without additional intervention of drivers, vehicles need to be connected to a wireless link and data transmission for downloading update software, which may cause additional costs.

Although such a software update method can simultaneously update software of many vehicles, a vehicle needs to be located in a designated place such as a repair shop or center. A step of directly locating an external device around the vehicle and authenticating a gateway connected to the external device is required. In addition, additional steps for software updates are needed since software updates require an intervention of a driver or a software update operator.

Furthermore, the software update method does not install a software update received and temporarily stored in a terminal. When a software update registered in a server is present, the software update method downloads the software update registered in the server without checking version information of temporarily stored software or the software update registered in the server. Accordingly, a software transmission necessary to update software of terminals is expensive.

SUMMARY

An object of the present disclosure devised to solve the problem is to provide a software update by comparing version information of software temporarily stored in a terminal or software installed in the terminal with version information of a software update registered in a server and deleting the temporarily stored software or the installed software.

In an aspect of the present disclosure to accomplish the object, a system for providing software update includes: a server in which software updates are registered; and a terminal for receiving version information of a software update from the server and performing software update on the basis of the received version information of the software update, wherein the server includes a version information checking unit for collecting version information of software temporarily stored in the terminal or version information of software installed in the terminal and comparing the version information of the temporarily stored software or the version information of the installed software with the version information of the software update to determine whether to transmit the software update to the terminal.

When a software update of a higher version is received from the server, the terminal may overwrite the software temporarily stored therein with the software update of the higher version.

When a software update of the higher version is received from the server, the terminal may delete a pre-received software update and receive and install the software update of the higher version, wherein, upon reception of a software update having the same version as a software update interrupted during reception from the server, the terminal resumes download of the software update and installs the software update.

The version information checking unit may send, to the terminal, a message indicating that the version of the software update registered in the server is identical to or lower than the version of the software temporarily stored or installed in the terminal, on the basis of the version information of the software temporarily stored or installed in the terminal.

The terminal may install the temporarily stored software on the basis of the message indicating that the version of the software update registered in the server is identical to or lower than the version of the temporarily stored software.

The version information checking unit may transmit the software update registered in the server to the terminal upon determining that the version of the software update registered in the server is higher than the version of the software temporarily stored or installed in the terminal.

When a software update of the higher version is present in the server, the terminal may delete the temporarily stored software or installed software and install the software update received from the server.

The terminal may indicate that the software installed therein is a newest version when the version of the installed software is the same as the software update registered in the server.

In another aspect of the present disclosure, a method of providing software update includes: a server collecting version information of software temporarily stored in a terminal or version information of software installed in the terminal, or the terminal providing the version information; when a software update is registered in the server, comparing version information of the registered software update with the version information of the software temporarily stored in the terminal or the version information of the software installed in the terminal; and determining whether to transmit the software update to the terminal according to a version information comparison result.

The method may further include sending, to the terminal, a message indicating that the version of the software update registered in the server is identical to or lower than the version of the software temporarily stored or installed in the terminal, on the basis of the version information of the software temporarily stored or installed in the terminal.

The method may further include installing the temporarily stored software on the basis of the message indicating that the version of the software update registered in the server is identical to or lower than the version of the software temporarily stored or installed in the terminal.

The method may further include transmitting the software update registered in the server to the terminal upon determining that the version of the software update registered in the server is higher than the version of the software temporarily stored or installed in the terminal.

The method may further include deleting the software temporarily stored or installed in the terminal and installing a software update of a higher version received from the server when the software update of the higher version is present in the server.

The method may further include indicating that the installed software is a newest version when the version of the installed software is the same as the version of the software update registered in the server.

In another aspect of the present disclosure, a terminal includes: a communication unit for wirelessly exchanging data with a server; a storage unit for storing a software update being received or received from the server through the communication unit, the software update being installed in the storage unit; and a controller for checking version information of the software update through the communication unit and performing software update on the basis of the version information of the software update according to a checking result, wherein the controller deletes a software update of a lower version, partially received and stored in the storage unit, or an entirely received software update of the lower version, and instructs the terminal to receive and install the software update of a higher version.

When the software update of the higher version is received from the server, the controller may overwrite the software temporarily stored in the storage unit with the software update.

Upon reception of a software update having the same version as a software update interrupted during reception from the server, the terminal may resume download of the software update and installs the software update.

In another aspect of the present disclosure, a method of installing a software update includes: asking a server for version information of a software update being received from the server or received or installed software; deleting a software update of a lower version, partially received and stored in a terminal, or a received software update of the lower version, upon reception of a software update of a higher version corresponding to the version information; and receiving and installing the software update of the higher version.

The method may further include overwriting temporarily stored software with the software update of the higher version upon reception of the software update of the higher version from the server.

The method may further include, upon reception of a software update having the same version as a software update interrupted during reception from the server, resuming download of the software update and installing the software update.

DETAILED DESCRIPTION

The present disclosure will now be described in more detail through some non-limiting exemplary embodiments with reference to the accompanying drawings so that the present disclosure can be easily understood and realized by those skilled in the art. The same reference numbers will be used throughout this specification to refer to the same or like parts. In the following description of the present disclosure, a detailed description of known functions and configurations incorporated herein will be omitted when it may obscure the subject matter of the present disclosure. Some features shown in figures are enlarged, reduced or simplified for facilitation of description, and figures and components thereof are not necessarily illustrated with proper proportions. However, such details will be readily understood by those skilled in the art.

Figure 1:
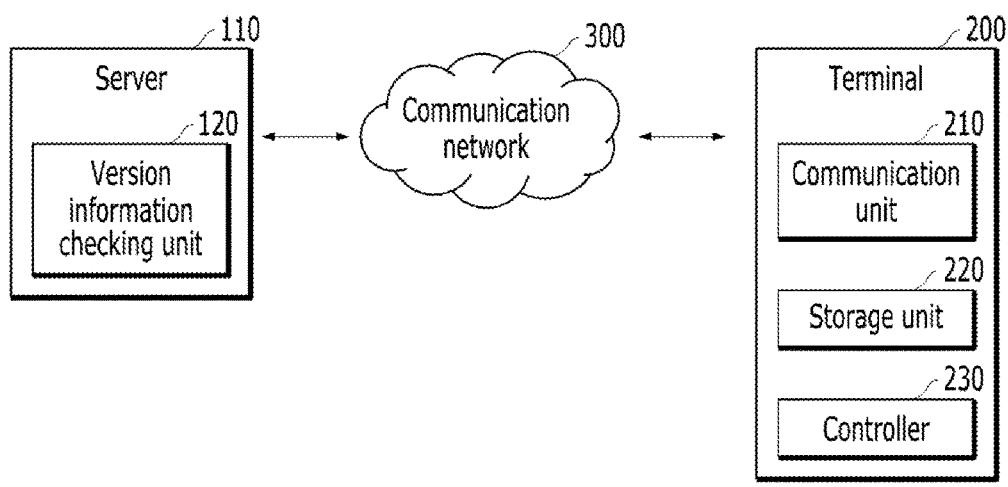
FIG. 1 is a block diagram of a system for providing software updates according to an exemplary embodiment of the present disclosure.
Figure 2:
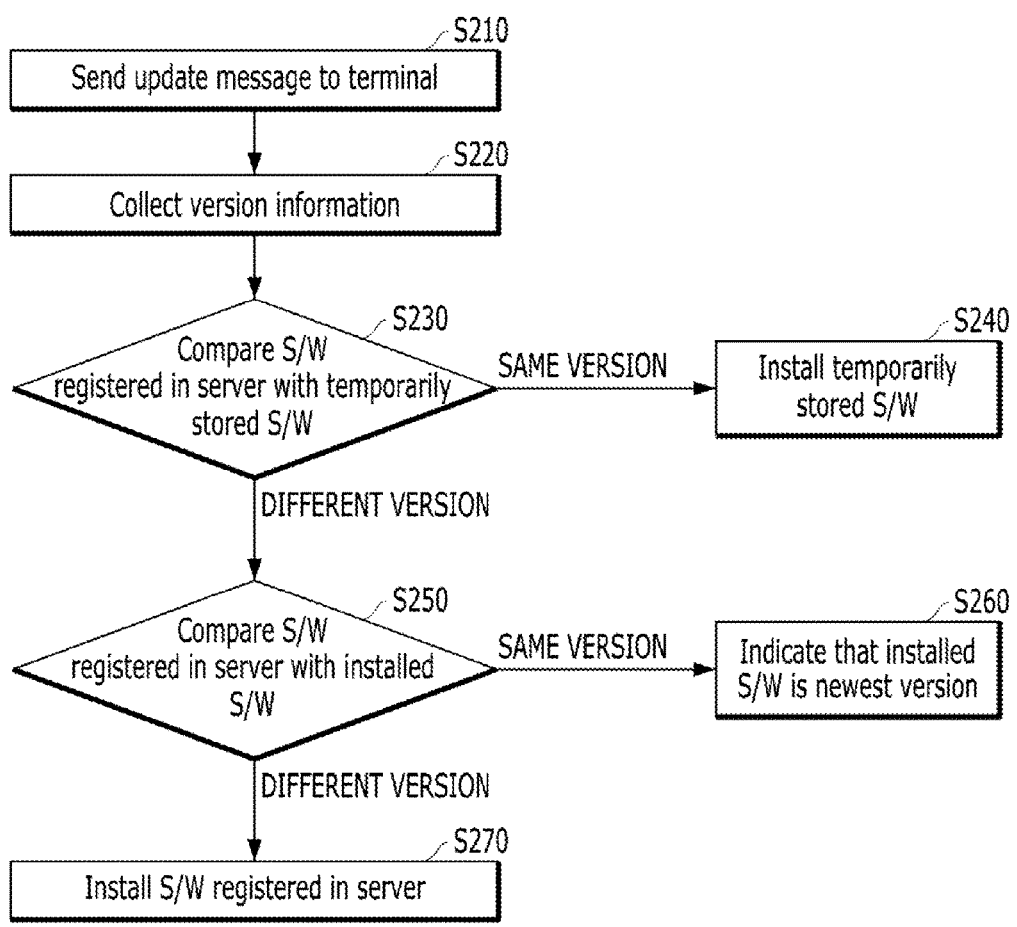
FIG. 2 is a flowchart illustrating a method of providing software updates according to an exemplary embodiment of the present disclosure.
Figure 3:
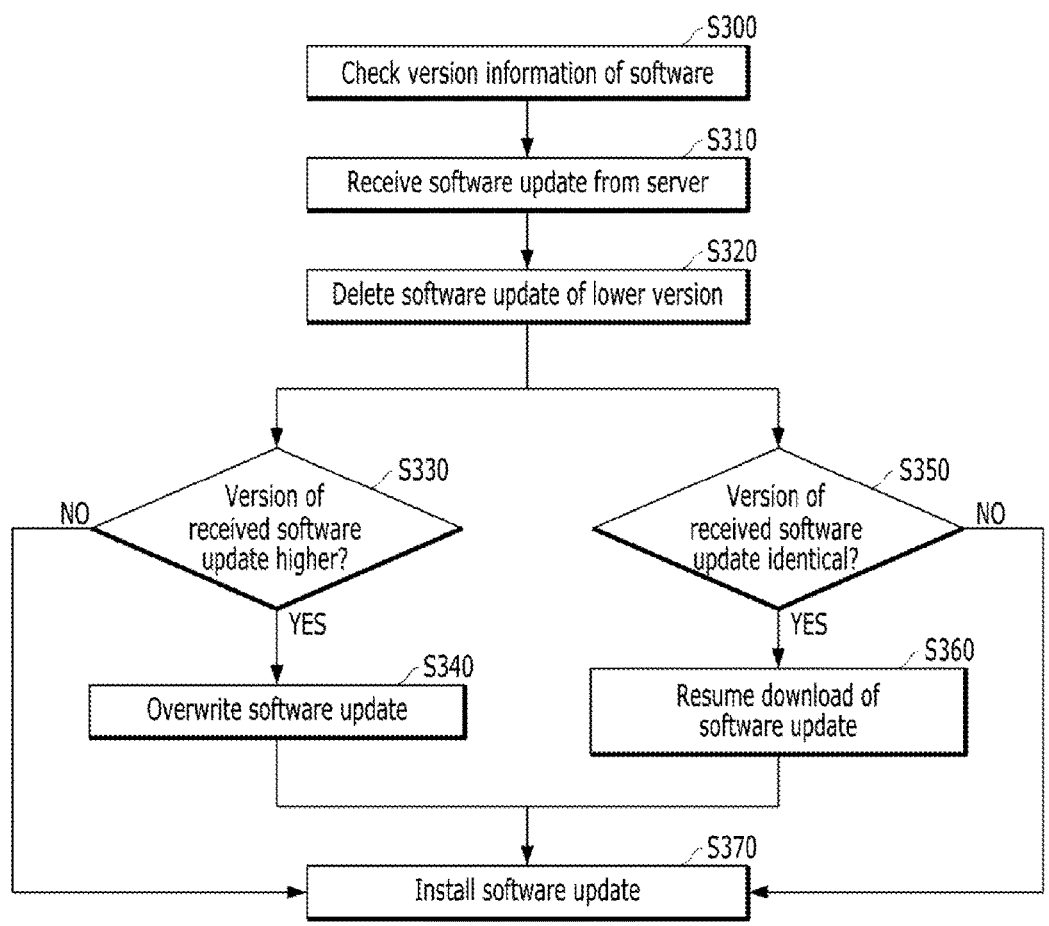
FIG. 3 is a flowchart illustrating a method of installing software updates according to an exemplary embodiment of the present disclosure.

FIG. 1 is a block diagram of a system for providing software updates according to an exemplary embodiment of the present disclosure, FIG. 2 is a flowchart illustrating an exemplary embodiment of a method of providing software updates according to the present disclosure and FIG. 3 is a flowchart illustrating a method of installing software updates according to an exemplary embodiment of the present disclosure.

As shown in FIG. 1, some implementations of a system 100 for providing software updates include a server 110, a version information checking unit 120, and a terminal 200 for receiving a software update provided by the server 110 and updating software.

Here, the terminal 200 includes a communication unit 210, a storage unit 220 and a controller 230.

In addition, the system 100 includes a communication network 300 for interconnecting the server 110 and the terminal 200.

The server 110 may store software updates registered by an administrator and transmit the software update to the terminal 200 included in a vehicle.

The software being updated may be software for updating various electronic systems of a vehicle, for example, a power steering module, a door locking system, an air-conditioning system and a navigation system.

Accordingly, the server 110 may correspond to a computing device connectable to the terminal 200 via the communication network 300 and may be managed by a software update distribution service provider.

In some embodiments, the server 110 can distribute the software update to the terminal 200 and provide an update file of the software such that the terminal 200 can update the corresponding software to a new version.

The version information checking unit 120 may compare software version information of the server 110 and the terminal 200 through a protocol connection with the terminal 200 and transmit a software update registered in the server 110 to the terminal 200.

To provide the software update to the terminal, the version information checking unit 120 may collect version information of software temporarily stored in the terminal or software installed therein. In addition, the version information checking unit 120 may collect version information of a software update registered in the server 110.

Accordingly, upon registration of a new software update in the server 110, the version information checking unit 120 may compare the collected version information of the temporarily stored software or installed software with the version information of the registered software update.

That is, when the version of software temporarily stored in the terminal 200 is higher than the version of the software update registered in the server 110, the version information checking unit 120 may send an installation message to the terminal 200 such that the terminal 200 installs the temporarily stored software.

In addition, when the version of software temporarily stored or installed in the terminal 200 is higher than the version of the software update registered in the server 110, the version information checking unit 120 may send a message indicating that the software temporarily stored or installed in the terminal 200 is the newest, or a newer, version.

The version information checking unit 120 may transmit the software update registered in the server 110 to the terminal 200 upon determining that the version of the software update is higher than the version of the software temporarily stored or installed in the terminal 200.

In another embodiment, when the software temporarily stored in the terminal 200 is the newest, or a newer, version, the server 110 may check a transfer rate corresponding to a file size of the temporarily stored software (e.g. a file transfer rate of the software corresponding to 30% when the transfer rate of the temporarily stored software is 70%) and complete a software update transmission corresponding to the checked transfer rate.

The terminal 200 may install the software update provided by the server 110.

When the version of the software installed in the terminal 200 is the same as the software update registered in the server, the terminal 200 may display a message indicating that the installed software is the newest, or a newer version on a display device (not shown) so as to notify the driver that the installed software is the newest, or a newer, version.

The terminal 200 may store the software update received from the server 110 through the communication unit 210 in the storage unit 220.

Here, the communication unit 210 is a device that executes a wireless communication function through a wireless network such as a mobile communication network, the Internet and a Wi-Fi network. However, the communication unit 210 is not limited thereto and may provide telematics which is a vehicle wireless Internet service.

The communication unit 210 according to the present disclosure may be primarily connected to the communication network 300 to interwork with the server 110 and transmit software version information to the server 110 or a software update received from the server 110.

When a software update of the same version as a software update previously received and stored in the storage unit 220 is received from the server 110, the terminal 200 may download the software update, add the downloaded software update to the stored software update and store the software update in the storage unit 220.

Accordingly, when a software update of the same version as software that is interrupted during reception, from among software temporarily stored in the terminal, is received from the server 110, the terminal 200 may resume download of the software update and automatically install the software under the control of the controller 230.

That is, upon reception of a software update of a higher version from the server 110, the terminal 200 can overwrite software temporarily stored therein with the software update or resume download of the software update, add the software update to the previously received software update and store the software update in the storage unit 220.

The storage unit 220 may temporarily store the software update transmitted from the server 110 and, when the software update is completed, automatically delete a software update of an old version and/or temporarily stored software under the control of the controller 230.

The controller 230 may control a selected system operation using pre-stored firmware and, when an error is generated in a specific system, generate error information and store the error information in the storage unit 220.

Accordingly, the terminal 200 can transmit a request for reprogramming of software of the specific system with respect to the error information to the server 110 to update the software of the specific system.

Upon arrival at a vehicle parking location or an update reservation time, the terminal 200 may access the server 110 through the communication network 300, download a software update and update software installed therein.

In another embodiment, the terminal 200 may transmit version information of a software update being received from the server or software that has been received or installed, to the server 110.

Accordingly, when a software update of higher version, corresponding to the transmitted version information, is received from the server 110, the terminal 200 may delete a software update of a lower version, which has been partially received or entirely received and stored in the storage unit 220, under the control of the controller 230, receive the software update of a higher version and install the software update of a higher version.

Thereafter, the terminal 200 may overwrite the temporarily stored software with the software update of a higher version received from the server 110.

When a software update of the same version as software interrupted during reception is received from the server 110, the terminal 200 may resume download of the software update and install the software update.

The communication network 300 executes a wireless communication function between the server 110 and the terminal 200 and may include a mobile communication network, the Internet, a Wi-Fi network or the like. However, the communication network 300 is not limited thereto and may be configured to provide telematics.

In addition, the terminal 200 may enter a sleep mode and switch a connection state with the server 110 to a standby state upon completion of software update.

A description will be given of a method of providing a software update and a method of installing a software update according to the aforementioned software update providing system 100.

As shown in FIG. 2, in some implementations the server 110 may send a message for a software update to the terminal 200 upon registration of new software update therein (S210).

The server 110 may collect version information of software temporarily stored in the terminal or version information of software installed in the terminal 200 and transmit the version information to the version information checking unit 120 (S220).

The version information checking unit 120 may compare version information of the software update registered in the server 110 with the version information of the software temporarily stored in the terminal 200 (S230).

Upon determining that the version of the software update registered in the server 110 is lower than the version of the software temporarily stored in the terminal 200, the version information checking unit 120 may send a message for instructing the terminal 200 to install the temporarily stored software in the terminal 200 such that the terminal 200 installs the temporarily stored software (S240).

The version information checking unit 120 may compare the version information of the software update registered in the server 110 with the version information of the software installed in the terminal 200 (S250).

When the version of the software installed in the terminal 200 is higher than the version of the software update registered in the server 110, the version information checking unit 120 may send a message indicating that the software installed in the terminal 200 is the newest, or a newer, version to the terminal 200 (S260).

When the version of the software update registered in the server 110 is higher than the version of the software installed in the terminal 200, the version information checking unit 120 may transmit the software update registered in the server 110 to the terminal 200 such that the terminal 200 installs the software update received from the server (270).

Referring to FIG. 3, in some implementations the terminal may ask the server 110 for version information of a software update being received from the server 110 or software that has been received or installed (S300).

The terminal 200 may receive a software update of higher version corresponding to the version information from the server 110 (S310).

Upon reception of the software update of a higher version from the server 110, the terminal 200 may delete a software update of a lower version, which has been partially received or entirely received and stored in the storage unit 220 according to a deletion instruction of the controller 230 (S320).

The terminal 200 may check version information of the software update received from the server 110 (S330).

The terminal 200 may overwrite software temporarily stored therein with the software update of a higher version upon reception of the software update of a higher version from the server 110 (S340).

The terminal 200 may check whether the version information of the software update received from the server 110 is the same as version information of a software update interrupted during reception (S350).

When the software update having the same version as the software update interrupted during reception is received from the server 110, the terminal 200 may resume download of the software update (S360).

The terminal 200 may receive the software update of a higher version from the server 110 and install the software update of a higher version under the control of the controller 230 (S370).

The method of providing a software update and the method of installing a software update according to the present disclosure determine whether the version of a software update registered in the server 110 is higher than the version of software temporally stored or installed in the terminal 200 through the version information checking unit 120, thereby determining whether to maintain software data, reducing communication costs and enhancing data reception efficiency.

Those skilled in the art will appreciate that the present disclosure may be carried out in other specific ways than those set forth herein without departing from the spirit and essential characteristics of the present disclosure. The above embodiments are therefore to be construed in all aspects as illustrative and not restrictive. The scope of the disclosure should be determined by the appended claims and their legal equivalents, not by the above description, and all changes coming within the meaning and equivalency range of the appended claims are intended to be embraced therein.

What is claimed is:

1. A system for providing a software update, comprising:
a server in which software updates are registered; and
a terminal receiving version information of a software update from the server and performing a software update on the installed software based on the basis of the received version information of the software update,
wherein the server includes a version information checking unit for collecting version information of software temporarily stored in the terminal and version information of software installed in the terminal and comparing the version information of the temporarily stored software and the version information of the software installed in the terminal with the version information of the software update to determine whether to transmit the software update to the terminal; and
transmitting the software update to the terminal.

2. The system according to claim 1, wherein, when a software update of a higher version is received from the server, the terminal overwrites the software temporarily stored therein with the software update of the higher version.

3. The system according to claim 2, wherein, when a software update of the higher version is received from the server, the terminal deletes the software temporarily stored in the terminal and receives and installs the software update of the higher version,
wherein, upon reception of a software update having the same version as the software temporarily stored in the terminal whose downloading was previously interrupted during reception from the server, the terminal resumes download of the software update and installs the software update.

4. The system according to claim 1, wherein the version information checking unit sends, to the terminal, a message indicating that the version of the software update registered in the server is identical to or lower than the version of the software temporarily stored or installed in the terminal, on the basis of the version information of the software temporarily stored or installed in the terminal.

5. The system according to claim 4, wherein the terminal installs the temporarily stored software on the basis of the message indicating that the version of the software update registered in the server is identical to or lower than the version of the temporarily stored software.

6. The system according to claim 4, wherein the version information checking unit transmits the software update registered in the server to the terminal upon determining that the version of the software update registered in the server is higher than the version of the software temporarily stored or installed in the terminal.

7. The system according to claim 6, wherein, when a software update of the higher version is present in the server, the terminal deletes the temporarily stored software or installed software and installs the software update received from the server.

8. The system according to claim 1, wherein the terminal indicates that the software installed therein is a newest version when the version of the installed software is the same as the software update registered in the server.

9. A method of providing a software update, comprising:
a server collecting version information of software temporarily stored in a terminal and version information of software installed in the terminal;

when a software update is registered in the server, the server comparing version information of the registered software update with the version information of the software temporarily stored in the terminal and the version information of the software installed in the terminal to determine whether to transmit the software update to the terminal; and transmitting the software update to the terminal according to a version information comparison result, wherein the terminal updating the installed software based on the software update.

10. The method according to claim 9, further comprising sending, to the terminal, a message indicating that the version of the software update registered in the server is identical to or lower than the version of the software temporarily stored or installed in the terminal, on the basis of the version information of the software temporarily stored or installed in the terminal.

11. The method according to claim 10, further comprising installing the temporarily stored software on the basis of the message indicating that the version of the software update registered in the server is identical to or lower than the version of the software temporarily stored or installed in the terminal.

12. The method according to claim 9, further comprising transmitting the software update registered in the server to the terminal upon determining that the version of the software update registered in the server is higher than the version of the software temporarily stored or installed in the terminal.

13. The method according to claim 12, further comprising deleting the software temporarily stored or installed in the terminal and installing a software update of a higher version received from the server when the software update of the higher version is present in the server.

14. The method according to claim 9, further comprising indicating that the installed software is a newest version when the version of the installed software is the same as the version of the software update registered in the server.

15. A terminal, comprising:
a communication unit for wirelessly exchanging data with a server;
a storage unit for storing a software update received or being received from the server through the communication unit, the software update being installed in the storage unit; and
a controller for checking version information of a software temporarily stored in the storage unit and version information of software installed in the terminal through the communication unit and performing a software update on the basis of the version information of the software update according to a checking result,
wherein the controller deletes a software update of a lower version, partially received and stored in the storage unit, or an entirely received software update of a lower version, and instructs the terminal to receive and install the software update of a higher version.

16. The terminal according to claim 15, wherein, when the software update of the higher version is received from the server, the controller overwrites the software temporarily stored in the storage unit with the software update.

17. The terminal according to claim 15, wherein, upon reception of a software update having the same version as the software temporarily stored in the terminal whose downloading was previously interrupted during reception from the server, the terminal resumes download of the software update and installs the software update.

* * * * *